United States Patent [19]

Guyton

[11] 4,435,052
[45] Mar. 6, 1984

[54] OPHTHALMIC TEST APPARATUS HAVING MAGNIFICATION COMPENSATION

[76] Inventor: David L. Guyton, 307 Somerset Rd., Baltimore, Md. 21210

[21] Appl. No.: 202,521

[22] Filed: Oct. 31, 1980

[51] Int. Cl.³ .............................................. A61B 3/02
[52] U.S. Cl. .................................................... 351/239
[58] Field of Search ..................................... 351/19–22, 351/26–30, 32–36, 222, 237, 239–243

[56] References Cited

U.S. PATENT DOCUMENTS

| | | | |
|---|---|---|---|
| 3,240,548 | 3/1966 | Biessels | 351/222 |
| 3,969,020 | 7/1976 | Lynn et al. | 351/28 X |
| 4,105,302 | 8/1978 | Tate, Jr. | 351/30 X |

OTHER PUBLICATIONS

Asher, "A New Cross Cylinder Method", *Oregon Optometrists*, vol. 34, No. 4, pp. 9–11, (1967).

*Primary Examiner*—F. L. Evans
*Attorney, Agent, or Firm*—Alan H. Spencer

[57] ABSTRACT

In apparatus for determining the refractive correction for a patient's eye, a plurality of similar test targets are presented to the patient simultaneously, with these test targets being viewed through different trial refractive corrections for the patient to choose between. Magnification differences produced by the different trial refractive corrections are compensated for by altering the size or shape of the different test targets, such that when magnified by the respective trial refractive correction, each test target appears of normal size and shape to the patient, not interfering with the patient's judgment of best clarity.

1 Claim, 8 Drawing Figures

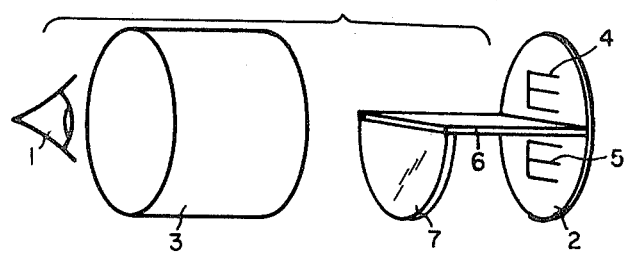 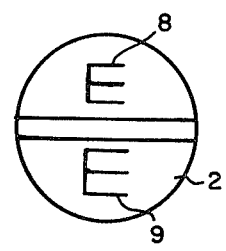
Fig. 1    Fig. 2
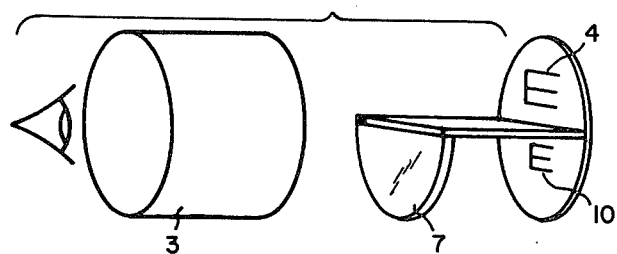 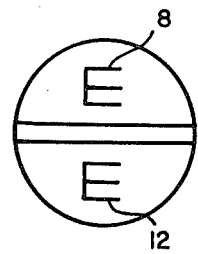
Fig. 3    Fig. 4
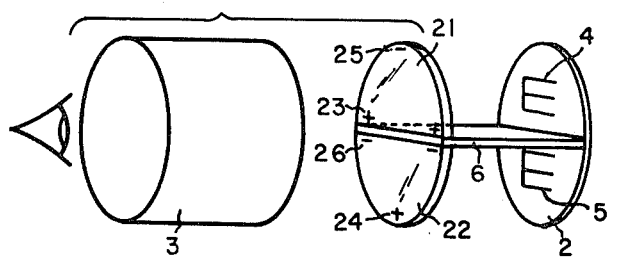 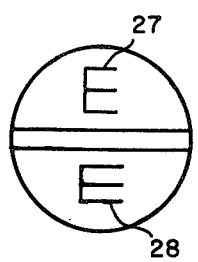
Fig. 5    Fig. 6
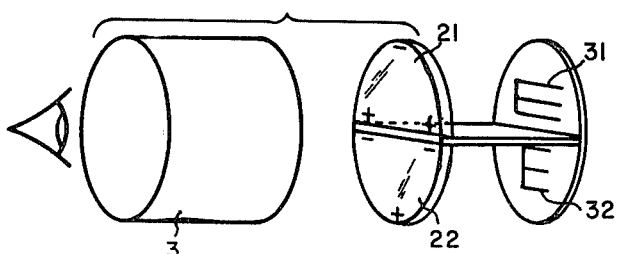 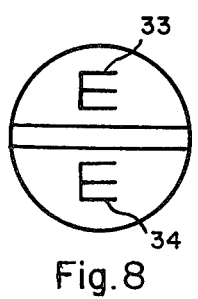
Fig. 7    Fig. 8

OPHTHALMIC TEST APPARATUS HAVING MAGNIFICATION COMPENSATION

BACKGROUND OF THE INVENTION

1. Field of the Invention

This invention relates generally to apparatus for determining the refractive correction for a patient's eye and relates more particularly to apparatus for simultaneous presentation of a plurality of optical corrections from which the patient may choose.

2. Discussion of the Prior Art

It is common practice in determining the refractive correction for a patient's eye to change the refractive correction by small amounts while asking a question such as "Which is better, 1 or 2?" To facilitate comparison of the two choices, several optical systems have been devised which produce a double image of a distant target, one of the two images being seen through one trial refractive correction, and the other of the two images being seen through a different trial refractive correction. The patient simply indicates which of the two images is more clear, and appropriate changes are made in the overall refractive correction for the eye until the final correction is obtained.

A major problem in comparing two different refractive corrections by viewing a single test target through each is that different magnifications are characteristically obtained through the two different corrections. With the small test targets which must be used for critical testing, differences in magnification are easily mistaken for small differences in blur, leading to error in the determination of the refractive correction.

U.S. Pat. No. 3,240,548 describes a doubling optical system for refractive testing wherein magnification differences are compensated for by careful choice of the lens components through which the two images are viewed. Similar magnification compensation by special lens design is described by Haynes, P.R., "A Homokonic Cross Cylinder for Refractive Procedures," Amer. J. Optom., Vol. 34, pp. 478-485 (1957). A problem is that special lens designs may produce differences in brightness of the two images, leading to error in choosing. This problem is discussed in U.S. Pat. No. 3,811,756, and by Luneburg, R. J., "Modified Simultantest—Validity," Optical J. and Rev. Optom., Vol. 108, No. 2, pp. 29-31 (Jan. 15, 1971). Further problems with special lens designs are complexity and cost, especially when short testing distances are used.

An alternate method for simultaneous presentation of two different trial refractive corrections is to provide two similar test targets in the patient's field of view and to place different lenses in front of each. This method is highly unusual, being described only by Asher, H. "A New Cross Cylinder Method," Oregon Optometrist, Vol. 34, No. 4, pp. 9-11 (1967). Again, magnification differences may be compensated for by special lens design, but an additional problem with this arrangement is that it may only be used with long testing distances.

Accordingly, it is an object of this invention, in systems wherein a plurality of test targets are viewed simultaneously, to provide an alternate and simpler method of compensating for magnification differences.

A further object of the invention is to provide a method of magnification compensation which is applicable to a variety of testing distances.

Other objects and advantages of the invention will become apparent from the following description.

SUMMARY OF THE INVENTION

A plurality of similar test targets are presented simultaneously to a patient's eye, with these test targets being viewed through different trial refractive corrections from which the patient is to choose. Magnification differences that arise are compensated for by altering the shapes or sizes of the different test targets such that when magnified by the respective trial refractive correction, each test target appears of normal size and shape. Such magnification compensation can be provided for different spherical refractive corrections by altering the overall size of the different test targets. Magnification compensation for different astigmatic trial refractive corrections is provided by altering the shape (or "meridional magnification") of the different test targets.

Details of the invention will become more readily apparent from the following description when taken in conjuction with the accompanying drawings.

IN THE DRAWINGS

FIG. 1 diagramatically illustrates refracting apparatus having simultaneously-viewed test targets, with different spherical trial refractive corrections, without compensation for magnification differences;

FIG. 2 illustrates the patient's view of the test targets in the apparatus of FIG. 1;

FIG. 3 diagramatically illustrates the refracting apparatus of FIG. 1 wherein compensation for magnification differences has been achieved according to the present invention;

FIG. 4 illustrates the patient's view of the test targets in the apparatus of FIG. 3;

FIG. 5 diagramatically illustrates refracting apparatus having simultaneously-viewed test targets, with different astigmatic trial refractive corrections, without compensation for magnification differences;

FIG. 6 illustrates the patient's view of the test targets in the apparatus of FIG. 5;

FIG. 7 diagramatically illustrates the refracting apparatus of FIG. 5 wherein compensation for magnification differences has been achieved according to the present invention;

FIG. 8 illustrates the patient's view of the test targets in the apparatus of FIG. 7.

DESCRIPTION OF THE PREFERRED EMBODIMENTS

Referring to the apparatus of FIG. 1, the patient's eye 1 views test chart 2 through schematic refractive correcting means 3. Schematic refractive correcting means 3 represents one of many optical systems known to the art which are capable of varying the spherical and astigmatic refractive correction for an eye. Test targets 4 and 5, drawn the same size, are situated on the respective top and bottom halves of test chart 2, with the halves divided by opaque septum 6. Spherical lens 7, having positive power, is attached to septum 6 such that the patient views test target 5 through lens 7. Positive lens 7 magnifies the image of test target 5 as seen by the patient, such that images 8 and 9 (of FIG. 4) of test targets 4 and 5 respectively are of different size.

Referring to FIG. 3, the apparatus of FIG. 1 is shown with test target 5 having been replaced by test target 10, smaller than test target 5. The magnification of test target 10 produced by positive lens 7 is now exactly correct to equalize the size of the images 8 and 12, as seen by the patient in FIG. 4.

Referring to FIG. 5, apparatus similar to that in FIG. 1 is illustrated except that astigmatic lenses 21 and 22 have been attached to septum 6 such that the patient views test targets 4 and 5 through astigmatic lenses 21 and 22 respectively. The powers of astigmatic lenses 21 and 22 are chosen to provide the opposite "cross cylinder" effect for test targets 4 and 5. The "cross cylinder" test is a well-known method of clinical testing for astigmatism. Every astigmatic lens with cross cylinder effect has two axes, a plus axis and a minus axis. The plus axes of lenses 21 and 22 are indicated by +'s 23 and 24, and the minus axes are indicated by −'s 25 and 26.

Astigmatic lenses 21 and 22 produce meridional magnification of test targets 4 and 5, resulting in images 27 and 28 respectively (in FIG. 6), as viewed by the patient. Images 27 and 28 are oppositely distorted, confusing to the patient, when trying to choose between minor differences in blur of images 27 and 28.

Referring to FIG. 7, the apparatus of FIG. 5 is illustrated except that test targets 4 and 5 have been replaced by test targets 31 and 32. Test targets 31 and 32 are distorted in appropriate directions relative to the meridional magnification produced by lenses 21 and 22, such that images 33 and 34 (in FIG. 8) are of normal shape and equal size as viewed by the patient.

Without being misled by magnification differences, the patient can compare the refractive blur of images 8 and 12 in FIG. 4, or of images 33 and 34 in FIG. 8, and thus indicate the necessary change to be made in refractive correcting means 3, according to standard techniques of refraction.

It shall be evident to those skilled in the art that the means of magnification compensation according to the present invention, for the purpose of simultaneous comparison of test images, are applicable to a variety of optical configurations and testing distances in addition to those herein illustrated. Such magnification compensation means used with additional optical configurations and testing distances are to be considered as coming within the scope of the following claims or range of equivalency to which they are entitled.

I claim:

1. Ophthalmic test apparatus comprising a plurality of similar test targets presented simultaneously to a patient's eye, with at least one of said test targets having associated optical means for varying the trial refractive correction through which said one test target is viewed by said eye, whereby said patient may choose from a plurality of trial refractive corrections, wherein the improvement comprises two test targets simultaneously presented, each of said test targets having associated optical means to vary the respective trial refractive correction to produce opposite cross-cylinder effect for said two test targets, said test targets having meridional magnification difference which compensates for the astigmatic magnification difference produced by said optical means.

* * * * *